United States Patent [19]

Brieden

[11] Patent Number: 5,744,606
[45] Date of Patent: Apr. 28, 1998

[54] PROCESS FOR THE PREPARATION OF OPTICALLY ACTIVE 3-QUINUCLIDINOL

[75] Inventor: Walter Brieden, Glis, Switzerland

[73] Assignee: Lonza AG, Gampel/Valais, Switzerland

[21] Appl. No.: 783,893

[22] Filed: Jan. 16, 1997

[30] Foreign Application Priority Data

Jan. 19, 1996 [CH] Switzerland .................. 0139/96

[51] Int. Cl.$^6$ .................. C07D 453/00; C07D 453/02
[52] U.S. Cl. .................................. 546/133
[58] Field of Search .................................. 546/133

[56] References Cited

FOREIGN PATENT DOCUMENTS

| 0370415 | 5/1990 | European Pat. Off. . |
|---|---|---|
| 0 370 415 A1 | 6/1990 | European Pat. Off. . |
| 0564406 | 6/1993 | European Pat. Off. . |
| 0 564 406 A1 | 10/1993 | European Pat. Off. . |
| 0577253 | 1/1994 | European Pat. Off. . |
| 0577394 | 1/1994 | European Pat. Off. . |
| 0667350 | 8/1995 | European Pat. Off. . |
| WO 93/06098 | 4/1993 | WIPO . |

OTHER PUBLICATIONS

Chemical Abstracts, vol. 92, No. 5, Feb. 4, 1980, Columbus, Ohio, U.S., Abstract No. 41726.

Primary Examiner—Alan L. Rotman
Attorney, Agent, or Firm—Fisher, Christen & Sabol

[57] ABSTRACT

Optically active 3-quinuclidinol is obtained by the asymmetric hydrogenation of 3-quinuclidinone, its Lewis acid adducts or its tertiary or quaternary salts, for example, 1-(diphenylmethyl)-3-oxoquinuclidinium bromide. Rhodium/chiral diphosphine complexes with a metallocene structure are preferably used as catalysts. Optically active 3-quinuclidinol is a synthetic building block for pharmaceutical active substances ($M_1$ receptor agonists).

9 Claims, No Drawings

PROCESS FOR THE PREPARATION OF OPTICALLY ACTIVE 3-QUINUCLIDINOL

BACKGROUND OF THE INVENTION

1. Field of the Invention

The invention relates to a process for the preparation of optically active 3-quinuclidinol of the formula:

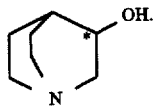
I

2. Background Art

Non-racemic 1-azabicyclo[2.2.2]octane with substituents in the 3-position, such as, 3-quinuclidinol (I), are synthetic building blocks for a number of pharmaceutical active substances (WO-A 93/06098, European Published Patent Application No. A-0370415). To date they have been obtained almost exclusively by solution of the racemates. This resolution entails considerable expense and gives the undesired enantiomer as a waste product.

BROAD DESCRIPTION OF THE INVENTION

The main object of the invention is to provide a route to and a process for producing non-racemic 3-quinuclidinol which do not involve resolution of the racemate. Other objects and advantages of the invention are set out herein or are obvious herefrom to one skilled in the art.

The objects and advantages of the invention are achieved by the processes of the invention.

The invention involves a process for the preparation of optically active 3-quinuclidinol of the formula:

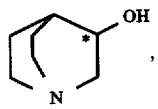

The process includes asymmetrically hydrogenating a quinuclidine derivative from the group consisting of 3-quinuclidinone of the formula:

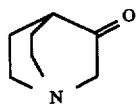
IIa and its adducts with Lewis acids, and the corresponding tertiary and quaternary salts of the general formula:

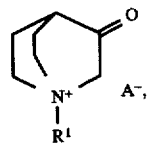
IIb wherein $R^1$ is hydrogen, a monoarylmethyl, a diarylmethyl or a triarylmethyl, and $A^-$ is the anion of an inorganic acid or an organic acid, in the presence of an optically active complex of rhodium, iridium or ruthenium with a chiral diphosphine as a ligand, acting as a catalyst, and cleaving the substituent $R^1$, if appropriate.

Preferably the boron trifluoride adduct of the formula:

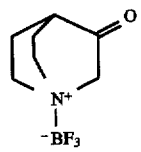
IIc is used as the adduct of 3-quinuclidinone (IIa) with a Lewis acid. Preferably a quaternary salt in which $R^1$ is o-bromobenzyl or diphenylmethyl, is used as the salt of 3-quinuclidinone. Preferably a bromide is used as the quaternary salt. Preferably a rhodium complex is used as the optically active complex and acts as a catalyst. Preferably the chiral diphosphine used is a diphosphine with a metallocene structure of the general formula:

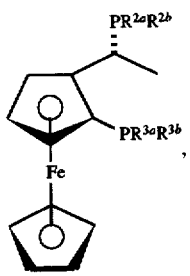
III wherein $R^{2a}$, $R^{2b}$, $R^{3a}$ and $R^{3b}$, independently of one another, are each $C_{1-12}$-alkyl, $C_{5-7}$-cycloalkyl or optionally substituted phenyl, or its mirror image. Preferably a diphosphine in which $R^{3a}$ and $R^{3b}$ are each phenyl and $R^{2a}$ and $R^{2b}$ are each tert-butyl or $R^{2a}$ and $R^{2b}$ are each cyclohexyl, is used as the diphosphine with a metallocene structure (III).

DETAILED DESCRIPTION OF THE INVENTION

It has been found that 3-quinuclidinone of the formula:

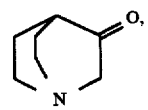
IIa its adducts with Lewis acids and the corresponding tertiary and quaternary salts of the general formula:

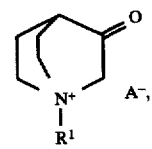
IIb wherein $R^1$ is hydrogen, a monoarylmethyl, a diarylmethyl or a triarylmethyl, and $A^-$ is the anion of an inorganic acid or an organic acid, can be asymmetrically hydrogenated in the presence of an optically active complex of rhodium, iridium or ruthenium with a chiral diphosphine, acting as a catalyst. The arylmethyl groups which can be present in the quaternary salts (IIb, $R^1 \neq H$) can be cleaved by hydrogenolysis in the same or a separate hydrogenation step.

Herein, mono-, di- and tri-arylmethyl groups are understood as meaning methyl groups substituted by one, two or three identical or different, substituted or unsubstituted, monocyclic or polycyclic aromatic groups. Examples of monocyclic aromatic groups are phenyl, alkylated phenyls such as o-, m- and p-tolyl or the various isomeric xylyls, halogenated phenyls such as o-, m- and p-chlorophenyl or bromophenyl, and alkoxyphenyls such as o-, m- and p-methoxyphenyl. Examples of polycyclic aromatic groups are 1- and 2-naphthyl, fluorenyl, anthracenyl, phenanthrenyl and the corresponding alkyl, alkoxy or halogen derivatives. 3-Quinuclidinone is preferably used as an adduct with a Lewis acid, especially as the boron trifluoride adduct of the formula:

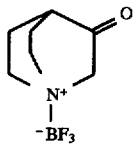

IIc or as a salt, especially as a quaternary salt. Suitable salts are those with inorganic acids, for example, the chlorides and bromides, as well as those with organic acids, for example, the acetates or mesylates.

Particularly good results have been achieved with bromide as the anion and with relatively bulky substituents $R^1$, for example, o-bromobenzyl or diphenylmethyl.

3-Quinuclidinone hydrochloride is commercially available; the free base can be obtained therefrom very easily by reaction with a strong base, for example, sodium hydroxide, and subsequent extraction. The adducts with Lewis acids can be prepared simply by adding the Lewis acid, for example, boron trifluoride or boron trifluoride etherate, to a solution of 3-quinuclidinone. The tertiary salts are correspondingly obtainable by adding a (Brønsted) acid. The quaternary salts can be prepared in conventional manner by reaction of 3-quinuclidinone with an alkylating agent, for example, benzyl chloride, benzyl bromide or diphenylmethyl bromide, optionally followed by anion exchange.

Rhodium complexes are preferably used as optically active complexes acting as catalysts. They are advantageously prepared in situ from a suitable precursor complex and the chiral diphosphine. An olefin complex is preferably used as the precursor complex. The commercially available bis(1,5-cyclooctadiene)dirhodium(I) dichloride ([Rh(COD)Cl]$_2$) is particularly preferred; it is advantageously reacted with the chiral diphosphine in a molar ratio of 1:2.

Examples of suitable chiral diphosphine ligands are 1,4-bis(diphenylphosphino)-1,4-dideoxy-2,3-o-isopropylidenethreitol ("DIOP"),2,2'-bis(diphenylphosphino)-1,1'-binaphthalene ("BINAP"), (R*,R*)-4-diphenylphosphino-2-(diphenylphosphinomethyl)pyrrolidine ("PPM") and (R*,R*)-2,3-bis(diphenylphosphino)butane ("Chiraphos"). These ligands are commercially available, for example, from Fluka.

Particularly preferred chiral diphosphines are those with a metallocene structure, for example, the disubstituted ferrocenes of the general formula:

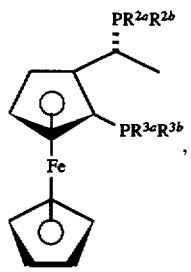

III wherein $R^{2a}$, $R^{2b}$, $R^{3a}$ and $R^{3b}$, independently of one another, are each $C_{1-12}$-alkyl, $C_{5-7}$-cycloalkyl or optionally substituted phenyl, and their mirror image.

(R)-1-[(S)-2-(diphenylphosphino)ferrocenyl]ethyl-di-tert-butylphosphine ($R^{2a}=R^{2b}$=tert-butyl, $R^{3a}=R^{3b}$=phenyl, IIIa) and (R)-1-[(S)-2-(diphenylphosphino)-ferrocenyl]ethyl-dicyclohexylphosphine ($R^{2a}=R^{2b}$=cyclohexyl, $R^{3a}=R^{3b}$=phenyl, IIIb), and their mirror images, are very particularly preferred. The preparation of these ligands is described in European Published Patent Application No. A-0564406. Good optical yields of up to 60 percent ee have been achieved with these ligands, even for high educt/catalyst molar ratios of the order of magnitude of $10^3$.

The hydrogenation is advantageously carried out at a temperature of 0° to 100° C. and a hydrogen pressure of 1 to 150 bar. Examples of suitable solvents are lower alcohols such as methanol, esters such as ethyl acetate, ketones such as acetone, and aromatic hydrocarbons such as toluene.

When cleavage of the substituent $R^1$ is appropriate, any useful or conventional cleavage agent or means can be used.

The following examples illustrate how the process according to the invention is carried out.

EXAMPLE 1

3-Quinuclidinone 300 g (1.856 mol) of 3-quinuclidinone hydrochloride (Fluka) was added at 40° C. to a solution of 300 g (7.50 mol) of sodium hydroxide in 1 liter of water and the solution formed was cooled to 20° C. It was then extracted three times with 400 ml of ethyl acetate and the combined organic extracts were dried over magnesium sulfate. After evaporation, 220 g (95 percent) of 3-quinuclidinone was obtained in the form of a light beige solid. Other data concerning the product was:

M.p.: 146°–147° C.
$^1$H NMR(CDCl$_3$, 300 MHz):

$\delta =$ 3.39–3.19(m, 2H);
3.10–2.81(m, 4H);
2.50–2.43(m, 1H);
2.10–1.90(m, 4H).

EXAMPLE 2

3-Quinuclidinone hydrobromide 21.8 g (167 mol) of 62 percent hydrobromic acid was added dropwise to a solution of 19.0 g (152 mol) of 3-quinuclidinone in 50 ml of water and the reaction mixture was evaporated to dryness. The residue was suspended in 100 ml of tetrahydrofuran, filtered off on a frit and washed with 50 ml of tetrahydrofuran. After drying, 30.5 g (98 percent) of 3-quinuclidinone hydrobromide were isolated in the form of white crystals.

EXAMPLE 3

3-Quinuclidinone/boron trifluoride adduct 36.5 g (257 mmol) of boron trifluoride etherate was added dropwise over 40 minutes to 33.2 g (266 mmol) of 3-quinuclidinone in 100 ml of diethyl ether and 250 ml of n-hexane. The solid which precipitated out was filtered off on a frit after 1 hour and dried to give 50.2 g (98 percent) of 3-quinuclidinone/boron trifluoride adduct in the form of a white powder. NMR data for the product: The spectra were run in d$_4$-methanol. The reversible addition of a solvent molecule onto the carbonyl group resulted in the formation of a hemiacetal, whose signals are indicated below.

¹H NMR(400 MHz):

δ = 4.00–3.98(m, 2H);
3.63–3.52(m, 2H);
3.50–3.42(m, 2H);
2.74–2.70(m, 1H);
2.37–2.27(m, 2H);
2.24–2.13(m, 2H).

¹³C NMR(100 MHz):

δ = 96.42(s);
61.07(t);
47.53(t);
47.23(t);
30.71(d);
20.38(t);
20.05(t).

(Only the multiplicities resulting from direct ¹H—¹³C couplings are indicated.)

EXAMPLE 4

1-Benzyl-3-oxoquinuclidinium chloride 62.3 g (492 mmol) of benzyl chloride was added dropwise over 30 minutes to 61.6 g (492 mmol) of 3-quinuclidinone in 250 ml of acetonitrile and the suspension formed was filtered through a frit after 2 hours at 25° C. Washing with acetonitrile (2×100 ml) and drying gave 115.0 g (93 percent) of 1-benzyl-3-oxoquinuclidinium chloride in the form of white crystalline solid. Other data concerning the product was:

¹H NMR(DMSO-d₆, 400 MHz):

δ = 7.62–7.56(m, 2H);
7.55–7.50(m, 3H);
4.75(s, 2H)
4.29(s, 2H);
3.78–3.60(m, 4H);
2.70–2.66(m, 1H);
2.29–2.40(m, 2H);
2.12–2.02(m, 2H).

EXAMPLE 5

1-Benzyl-3-oxoquinuclidinium bromide 40.4 g (236 mmol) of benzyl bromide was added dropwise over 15 minutes to 29.5 g (236 mmol) of 3-quinuclidinone in 120 ml of acetonitrile and the suspension formed was filtered through a frit after 2 hours at 25° C. Washing with n-hexane (2×50 ml) and drying gave 65.3 g (93 percent) of 1-benzyl-3-oxoquinuclidinium bromide in the form of a white crystalline solid. Other data concerning the product was:

¹H NMR(DMSO-d₆, 400 MHz):

δ = 7.64–7.59(m, 2H);
7.56–7.50(m, 3H);
4.82(s, 2H);
4.34(s, 2H);
3.82–3.73(m, 2H);
3.73–3.64(m, 2H);
2.71–2.67(m, 1H);
2.32–2.22(m, 2H)}
2.13–2.01(m, 2H).

¹³C NMR(DMSO-d₆, 100 MHz):

δ = 202.49;
133.01;
130.28;
128.96;
127.08;
65.92;
64.42;
53.61;
37.29;
20.65.

EXAMPLE 6

1-(4-Methoxybenzyl)-3-oxoquinuclidinium bromide 1.57 g (10.0 mmol) of 4-methoxybenzyl chloride was added to 1.25 g (10.0 mmol) of 3-quinuclidinone in 10 ml of acetonitrile and the suspension formed was filtered through a frit after 30 minutes. Washing with n-hexane and drying gave 2.33 g (83 percent) of 1-(4-methoxybenzyl)-3-oxoquinuclidinium bromide in the form of a white crystalline solid. Other data concerning the product was:

¹H NMR(CDCl₃, 400 MHz):

δ = 7.65–7.61("d", 2H);
6.95–6.91("d", 2H);
5.23(s, 2H);
4.66(s, 2H);
4.19–4.10(m, 2H);
4.08–3.98(m, 2H);
3.82(m, 3H);
2.79–2.75(m, 1H);
2.40–2.30(m, 2H);
2.28–2.17(m, 2H).

EXAMPLE 7

1-(Diphenylmethyl)-3-oxoquinuclidinium bromide 26.0 g (100 mmol) of bromodiphenylmethane (~95 percent) was added to 12.5 (100 mmol) of 3-quinuclidinone in 100 ml of acetonitrile, with stirring, and the suspension formed was filtered through a frit after 24 hours. Washing with diethyl ether (100 ml) and drying gave 32.0 g (86 percent) of 1-(diphenylmethyl)-3-oxoquinuclidinium bromide in the form of a white crystalline solid. Other data concerning the product was:

¹H NMR(CDCl₃, 400 MHz):

δ = 7.99–7.94(m, 4H);
7.57–7.46(m, 6H);
6.32(s, 1H);
4.28(s, 2H);
3.83–3.65(m, 4H);
2.69–2.66(m, 1H);
2.30–2.20(m, 2H);
2.13–2.03(m, 2H).

EXAMPLE 8

(S) -3-Quinuclidinol 30.0 g (186 mmol) of 3-quinuclidinone hydrochloride, 18.3 mg (0.0371 mmol) of bis(1,5-cyclooctadiene)dirhodium(I) dichloride, 40.3 mg (0.0743 mmol) of (R)-1-[(S)-2-(diphenylphosphino)ferrocenyl]ethyl-di-tert-butylphosphine (IIIa, corresponding to an educt/catalyst molar ratio of 2500) and 300 ml of degassed methanol were introduced into an autoclave (450 ml) under argon. The reaction mixture was hydrogenated for 19 hours at 70° C. and 50 bar of H₂. It was evaporated and the residue was dissolved in 250 ml of 2N hydrochloric acid. After extraction twice with 40 ml of dichloromethane, the pH was adjusted to 14 with sodium hydroxide solution (30 percent) and the mixture was evaporated. The residue was refluxed with 350 ml of ethyl acetate and filtered off hot. The aqueous phase was separated off and the organic phase was evaporated. Recrystallization from ethyl acetate (150 ml) gave 22.3 (94 percent) of (S)-3-quinuclidinol with 24 percent ee. Other data concerning the product was:

$[\alpha]_D^{25} = +11.0 (c=2, 1N\ HCl)$

EXAMPLE 9

(R)-3-Quinuclidinol 100 g (268 mmol) of 1-(diphenylmethyl)-3-oxoquinuclidinium bromide, 66 mg (0.133 mmol) of bis(1,5-cyclooctadiene)dirhodium(I) dichloride, 145 mg (0.267 mmol) of (S)-1-[(R)-2-(diphenylphosphino)ferrocenyl] ethyl-di-tert-butylphosphine (IIIa, mirror image; corresponding to an educt/catalyst molar ratio of 1000) and 500 ml of degassed methanol were introduced into an autoclave (1 liter) under argon. The reaction mixture was hydrogenated for 19 hours at 75° C. and 10–14 bar of H₂. The mixture was then cooled, filtered and evaporated. The residue was taken up with 200 ml of water and 100 ml of ethyl acetate and the aqueous phase was washed again twice with 50 ml of ethyl acetate. The aqueous phase was adjusted to pH 14 with sodium hydroxide solution (30 percent) and evaporated to dryness. The residue was extracted four times with 100 ml of dichloromethane and the combined organic extracts were dried over MgSO₄ and evaporated to give 33.0 g (96.6 percent) of (R)-3-quinuclidinol in the form of a white crystalline solid. Recrystallization from ethyl acetate gave 28.3 g (83 percent) of (R)-3-quinuclidinol with 58 percent ee. Other data concerning the product was:

$[\alpha]_D^{25} = -26.1 (c=2, 1N\ HCl)$

EXAMPLE 10

(S)-3-Quinuclidinol

In an autoclave (160 ml), a solution of 200 mg (0.41 mmol) of bis(1,5-cyclooctadiene)dirhodium(I) dichloride and 480 mg (0.81 mmol) of (R)-1-[(S)-2-diphenylphosphino)ferrocenyl]ethyl-dicyclohexylphosphine (IIIb, corresponding to an educt/catalyst molar ratio of 50) in 70 ml of degassed methanol was added to 5.00 g (40 mmol) of 3-quinuclidinone under argon. The mixture was hydrogenated for 22 hours at 75° C. and 50 bar of H₂. After evaporation of the reaction solution, the pH was adjusted to 1 with 1N hydrochloric acid and the mixture was extracted three times with 50 ml of dichloromethane. The aqueous phase was adjusted to pH 14 with sodium hydroxide solution (30 percent) and evaporated to dryness. The residue was extracted four times with 100 ml of dichloromethane and the combined organic extracts were dried over MgSO₄ and evaporated to give 3.40 g (67 percent) of (S)-3-quinuclidinol in the form of a white crystalline solid. Recrystallization from ethyl acetate gave 2.65 g (52 percent) of (S)-3-quinuclidinol with 7 percent ee. Other data concerning the product was:

$[\alpha]_D^{23} = +3.2 (c = 2, 1\ N\ HCl)$

¹H NMR(CD₃OD, 400 MHz):

δ = 3.87–3.82(m, 1H);
3.13–3.05("ddd", 1H);
2.90–2.81(m, 1H);
2.80–2.70(m, 2H);
2.69–2.60(m, 1H);
2.58–2.51("dt", 1H);
2.02–1.92(m, 1H);
1.83–1.77(m, 1H);
1.76–1.68(m, 1H);
1.58–1.47(m, 1H);
1.45–1.36(m, 1H).

¹³C NMR(CD₃OD, 100 MHz):

δ = 68.16;
58.17;
48.13;
47.06;
29.08;
25.28;
19.62.

EXAMPLES 11 to 28

These examples were carried out analogously to Examples 8 to 10 with [Rh(COD)Cl]₂ as the precursor complex. The results are collated in Table 1 below. For each example, the Table indicates the educt with formula number and, where appropriate, the variable substituents, the chiral diphosphine ligand with its absolute configuration (IIIa=(R) -1-[(S)-2-(diphenylphosphino)ferrocenyl]ethyl-di-tert-butylphosphine, IIIb=(R)-1-[(S)-2-(diphenylphosphino)ferrocenyl]ethyl-dicyclohexylphosphine, the solvent, the educt/catalyst molar ratio (E/C), the specific rotation of the product and its optical purity (as the ee value) and the configuration of the preferentially formed enantiomer.

TABLE 1

| Example | Educt | Ligand | Solvent | E/C | $[\alpha]_D$ | ee (Config.) |
|---------|-------|--------|---------|-----|--------------|--------------|
| 11 | IIa | IIIa | Toluene | 50 | +0.4 | <1% (S) |
| 12 | IId | IIIa | MeOH | 50 | +5.3 | 12% (S) |

TABLE 1-continued

| Example | Educt | Ligand | Solvent | E/C | [α]_D | ee (Config.) |
|---|---|---|---|---|---|---|
| 13 | IId | IIIb | MeOH | 50 | +8.1 | 18% (S) |
| 14 | IId | IIIa | EtOA⁻ c | 500 | +0.5 | <1% (S) |
| 15 | IIb(R¹ = C₆H₅CH₂, A⁻ = Cl⁻) | IIIa | MeOH | 2500 | +14.1 | 31% (S) |
| 16 | IIb(R¹ = C₆H₅CH₂, A⁻ = Br⁻) | IIIa | MeOH | 2500 | +22.4 | 50% (S) |
| 17 | IIb(R¹ = C₆H₅CH₂, A⁻ = Br⁻) | IIIb | MeOH | 250 | +16.9 | 38% (S) |
| 18 | IIb(R¹ = o-BrC₆H₄CH₂, A⁻ = Br⁻) | IIIa | MeOH | 1000 | +23.9 | 53% (S) |
| 19 | IIb(R¹ = H, A⁻ = Cl⁻) | IIIb | MeOH | 1550 | +12.1 | 27% (S) |
| 20 | IIb(R¹ = H, A⁻ = Cl⁻) | IIIa | MeOH | 5000 | +10.7 | 24% (S) |
| 21 | IIb(R¹ = H, A⁻ = Br⁻) | IIIa | MeOH | 2500 | +12.9 | 28% (S) |
| 22 | IIb(R¹ = H, A⁻ = Cl⁻) | (S)-PPM | MeOH | 50 | −1.8 | 4% (R) |
| 23 | IIb(R¹ = H, A⁻ = Cl⁻) | (R,R)-DIOP | MeOH | 50 | +0.8 | 2% (S) |
| 24 | IIb(R¹ = H, A⁻ = Cl⁻) | (R)-BINA⁻ P | MeOH | 50 | +0.3 | <1% (S) |
| 25 | IIb(R¹ = H, A⁻ = Cl⁻) | (S)-Chiraphos | MeOH | 50 | −4.2 | 9% (R) |
| 26 | IIb(R¹ = H, A⁻ = OA⁻ c) | IIIa | MeOH | 1000 | +0.7 | 1% (S) |
| 27 | IIb(R¹ = H, A⁻ = MeSO₃) | IIIa | MeOH | 1000 | +2.0 | 4% (S) |
| 28 | IIb(R¹ = CHPh₂, A⁻ = Br⁻) | IIIb | MeOH | 2500 | +26.8 | 60% (S) |

What is claimed is:

1. A process for the preparation of optically active 3-quinuclidinol of the formula:

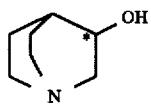

I comprising asymmetrically hydrogenating a quinuclidine derivative from the group consisting of 3-quinuclidinone tertiary and quaternary salts of the formula:

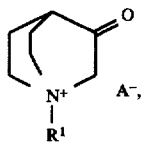

IIb wherein R¹ is hydrogen, a monoarylmethyl, a diarylmethyl or a triarylmethyl and A⁻ is the anion of an inorganic acid or an organic acid, in the presence of an optically active complex of rhodium, iridium or ruthenium with a chiral diphosphine as ligand, acting as a catalyst, in a suitable solvent, at a hydrogen pressure of 1 to 150 bar and at a temperature of 0° to 100° C., and cleaving the substituent R¹ if appropriate.

2. The process according to claim 1 wherein a quaternary salt in which R¹ is o-bromobenzyl or diphenylmethyl is used as the salt of 3-quinuclidinone.

3. The process according to claim 2 wherein a bromide is used as the quaternary salt.

4. The process according to claim 3, wherein a rhodium complex is used as the optically active complex acting as a catalyst.

5. The process according to claim 4 wherein the chiral diphosphine used is a diphosphine with a metallocene structure of the formula:

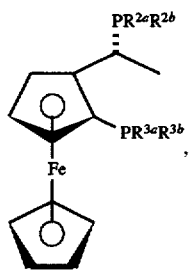

III wherein $R^{2a}$, $R^{2b}$, $R^{3a}$ and $R^{3b}$, independently of one another, are each $C_{1-12}$-alkyl, $C_{5-7}$-cycloalkyl or optionally substituted phenyl, or its mirror image.

6. The process according to claim 5 wherein a diphosphine in which $R^{3a}=R^{3b}$=phenyl and $R^{2a}=R^{2b}$=tert-butyl, or $R^{2a}=R^{2b}$=cyclohexyl, is used as the diphosphine with a metallocene structure (III).

7. The process according to claim 1 wherein a rhodium complex is used as the optically active complex acting as a catalyst.

8. The process according to claim 1 wherein the chiral diphosphine used is a diphosphine with a metallocene structure of the general formula:

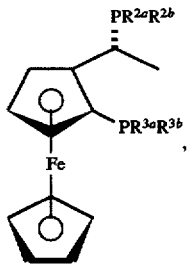

III wherein $R^{2a}$, $R^{2b}$, $R^{3a}$ and $R^{3b}$, independently of one another, are each $C_{1-12}$-alkyl, $C_{5-7}$-cycloalkyl or optionally substituted phenyl, or its mirror image.

9. The process according to claim 8 wherein a diphosphine in which $R^{3a}=R^{3b}$=phenyl and $R^{2a}=R^{2b}$=tert-butyl, or $R^{2a}=R^{2b}$=cyclohexyl, is used as the diphosphine with a metallocene structure (III).

* * * * *